(12) United States Patent
Lavanchy et al.

(10) Patent No.: US 12,232,535 B2
(45) Date of Patent: Feb. 25, 2025

(54) MOUTHPIECE WITH INNER AND OUTER TUBULAR SECTIONS

(71) Applicant: Philip Morris Products S.A., Neuchatel (CH)

(72) Inventors: Frederic Lavanchy, Chavornay (CH); Johannes Petrus Maria Pijnenburg, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 862 days.

(21) Appl. No.: 17/298,814

(22) PCT Filed: Dec. 4, 2019

(86) PCT No.: PCT/EP2019/083699
§ 371 (c)(1),
(2) Date: Jun. 1, 2021

(87) PCT Pub. No.: WO2020/115146
PCT Pub. Date: Jun. 11, 2020

(65) Prior Publication Data
US 2022/0030951 A1     Feb. 3, 2022

(30) Foreign Application Priority Data
Dec. 6, 2018    (EP) .................................... 18210859

(51) Int. Cl.
*A24F 7/02*   (2006.01)
*A24D 3/17*   (2020.01)
*A24F 40/485* (2020.01)

(52) U.S. Cl.
CPC .............. *A24F 40/485* (2020.01); *A24D 3/17* (2020.01)

(58) Field of Classification Search
CPC .... A24D 3/17; A24D 3/18; A24F 7/02; A24F 7/04
See application file for complete search history.

(56) References Cited

U.S. PATENT DOCUMENTS 2,954,778 A    10/1960  Lebert
4,413,641 A    11/1983  Dwyer, Jr. et al.
(Continued)

FOREIGN PATENT DOCUMENTS

CN    107684109 A      2/2018
EP    3 248 480 A1    11/2017
(Continued)

OTHER PUBLICATIONS

Office Action issued Jul. 27, 2022, in corresponding Japanese Patent Application No. 2021-531409 (with English Translation), 5 pages.
(Continued)

*Primary Examiner* — Cynthia Szewczyk
(74) *Attorney, Agent, or Firm* — Oblon, McClelland, Maier & Neustadt, L.L.P.

(57) ABSTRACT

A mouthpiece for attachment to a hollow tubular filter portion of an aerosol-generating article is provided, the mouthpiece including: an inner tubular section having a minimum outer diameter, which is smaller than an inner diameter of the hollow tubular filter portion; an outer tubular section having a maximum inner diameter, which is larger than an outer diameter of the aerosol-generating article; a central airflow channel arranged along a longitudinal axis of the mouthpiece, the airflow channel including a Venturi portion, the Venturi portion including an inlet portion and an outlet portion, the inlet portion being configured to converge in a downstream direction and the outlet portion being configured to diverge in a downstream direction; and a hinge section configured to attach the mouthpiece to an aerosol-generating device. A system including the mouthpiece, and (Continued)

a method for attaching the mouthpiece to the hollow tubular filter portion are also provided.

16 Claims, 4 Drawing Sheets

(56) References Cited

U.S. PATENT DOCUMENTS

| | | | |
|---|---|---|---|
| 4,517,996 A | 5/1985 | Vester | |
| 2009/0013994 A1 | 1/2009 | Jones et al. | |
| 2013/0032144 A1 | 2/2013 | Miller et al. | |
| 2014/0102451 A1 | 4/2014 | Jones et al. | |
| 2014/0216454 A1 | 8/2014 | Jones et al. | |
| 2014/0261490 A1* | 9/2014 | Kane | A24F 40/485 131/328 |
| 2015/0174343 A1 | 6/2015 | Muellinger et al. | |
| 2016/0081394 A1 | 3/2016 | Alarcon et al. | |
| 2017/0027226 A1 | 2/2017 | Mironov et al. | |
| 2017/0319795 A1 | 11/2017 | Jones et al. | |
| 2018/0116275 A1* | 5/2018 | Malgat | A24D 1/02 |
| 2018/0207374 A1 | 7/2018 | Jones et al. | |
| 2019/0124974 A1 | 5/2019 | Dimmick et al. | |
| 2019/0150516 A1* | 5/2019 | Shenkal | A24F 40/485 |

FOREIGN PATENT DOCUMENTS

| | | | |
|---|---|---|---|
| GB | 191110910 A | 4/1912 | |
| GB | 2 137 067 A | 10/1984 | |
| JP | 2010-532677 A | 10/2010 | |
| RU | 2 570 499 C2 | 12/2015 | |
| RU | 2 645 647 C1 | 2/2018 | |
| WO | WO 2009/009013 A2 | 1/2009 | |
| WO | WO 2013/054244 A1 | 4/2013 | |
| WO | WO 2013/132056 A1 | 9/2013 | |
| WO | WO 2014/183073 A1 | 11/2014 | |
| WO | WO 2015/053361 A1 | 4/2015 | |
| WO | WO 2015/117702 A1 | 8/2015 | |
| WO | WO-2017011419 A1 * | 1/2017 | .......... A24B 15/167 |
| WO | WO 2017/212284 A1 | 12/2017 | |
| WO | WO-2018144484 A1 * | 8/2018 | ............... A24D 3/17 |

OTHER PUBLICATIONS

Combined Russian Office Action and Search Report issued Sep. 22, 2021 in corresponding Russian Patent Application No. 2021119558/14(041074) (English Translation only), 10 pages.

International Search Report and Written Opinion issued on Feb. 20, 2020 in PCT/EP2019/083699 filed on Dec. 4, 2019.

* cited by examiner

MOUTHPIECE WITH INNER AND OUTER TUBULAR SECTIONS

The present invention relates to a mouthpiece for attachment to a hollow tubular filter portion of an aerosol-generating article.

It is known to provide an aerosol-generating device for generating an inhalable aerosol. Such devices may heat aerosol-forming substrate contained in an aerosol-generating article without burning the aerosol-forming substrate. The aerosol-generating article may have a rod shape for insertion of the aerosol-generating article into a heating chamber of the aerosol-generating device. A heating element may be arranged in or around the heating chamber for heating the aerosol-forming substrate once the aerosol-generating article is inserted into the heating chamber of the aerosol-generating device.

Typically, the generated aerosol exits the aerosol generating article through a mouthpiece. The mouthpiece may be part of the device or may be provided separately. The mouthpiece may be connected to the aerosol-generating article via an airflow channel or directly attached to the aerosol-generating article. In order to prevent loss of aerosol or an unintended pressure drop or the intake of ambient air in the junction between the mouthpiece and the aerosol-generating article, a good connection between the mouthpiece and the aerosol-generating article needs to be ensured.

It would be desirable to have a mouthpiece with an improved connection with an aerosol-generating article. Further, it would be desirable, if such a connection was robust and easy to make.

According to a first aspect of the invention there is provided a mouthpiece for attachment to a hollow tubular filter portion of an aerosol-generating article. The mouthpiece comprises an inner tubular section having a minimum outer diameter which is smaller than an inner diameter of the hollow tubular filter portion of the aerosol-generating article. The mouthpiece comprises an outer tubular section having a maximum inner diameter which is larger than an outer diameter of the aerosol-generating article.

The design of the mouthpiece according to the invention ensures a firm fit between the aerosol-generating article and the mouthpiece. Due to the specific minimum outer diameter of the inner tubular section and the maximum inner diameter of the outer tubular section of the mouthpiece, the hollow tubular filter portion of the aerosol-generating article may be inserted between the inner tubular section and the outer tubular section of the mouthpiece. In this way, the hollow tubular filter portion of the aerosol-generating article and therefore the aerosol-generating article can be securely held attached to the mouthpiece.

As used herein, the terms 'upstream' and 'downstream' are used to describe the relative positions of components, or portions of components, of the mouthpiece and the aerosol-generating article according to the invention in relation to the direction of air drawn through the mouthpiece and the aerosol-generating article during use thereof.

The mouthpiece preferably is configured as reusable mouthpiece to be used with multiple aerosol-generating articles. According to the invention, some of the functionality of the aerosol generating article can be transferred into the reusable mouthpiece. This means that elements that would be otherwise only used once can now be used multiple times. This means that the aerosol-generating articles can be simplified. This reduces the amount of waste from the single use articles that would be created otherwise. Particularly, the mouthpiece may be configured for reducing the temperature of the air containing vaporized aerosol-forming substrate flowing through the mouthpiece. An aerosol may thus be formed within the mouthpiece. Advantageously, this cooling functionality provided by the mouthpiece removes the requirement of providing a cooling section in aerosol-generating articles.

The specific configuration of the connection between the mouthpiece and the aerosol-generating article guarantees a secure connection between the mouthpiece and the aerosol-generating article. Thus, neither air nor vaporized aerosol-forming substrate, nor aerosol drawn through the aerosol-generating article towards the mouthpiece will leak between the aerosol-generating article and the mouthpiece. Also, any unintended dilution of the particle stream by ambient air that may be otherwise be entering from gaps between the aerosol-generating article and the mouthpiece can thus be prevented or at least reduced. The air will essentially completely or completely be drawn from the aerosol-generating article towards and through the mouthpiece during a puff.

After usage of the aerosol-generating article, the spent aerosol-generating article can be removed from the mouthpiece by pulling on the aerosol-generating article. A fresh aerosol-generating article can then be inserted into the mouthpiece.

The mouthpiece may comprise a stop arranged connecting the inner tubular section and the outer tubular section.

The stop may prevent over insertion of the mouthpiece into the hollow tubular filter portion of the aerosol-generating article. Similarly, the stop may prevent over insertion of the hollow tubular filter portion of the aerosol-generating article into the mouthpiece. Furthermore, the stop may be configured to prevent leakage of air between the aerosol-generating article and the mouthpiece. The stop may be configured as a connecting wall between the inner tubular section of the mouthpiece and the outer tubular section of the mouthpiece. The stop may be configured having a shape corresponding to the shape of a downstream end face of the hollow tubular filter portion of the aerosol-generating article. The stop may be configured for abutting the end face of the hollow tubular filter portion of the aerosol-generating article, once the hollow tubular filter portion has been inserted between the inner tubular section and the outer tubular section of the mouthpiece. The stop may have a circular or ring-shaped configuration. The stop may be configured as a smooth wall. A smooth wall may have the advantage that insertion and removal of the mouthpiece is easy. Also, the air-tightness of the fit between aerosol-generating article and mouthpiece may be best if both surfaces are smooth. Alternatively, it may be advantageous if a rough or structured surface may be employed in order to ensure the strength of the connection between aerosol-generating article and mouthpiece. The outer diameter of the aerosol generating article may be determining whether it is preferred to have a smooth or rough surface. For example, if the diameter is large, the contact/friction surface between the aerosol-generating article and the mouthpiece increases and the need for additional retention may be smaller.

The stop may comprise sealing means. The stop may be configured as or contain an O-ring. The stop may be configured such that an O-Ring may be inserted between the inner tubular section and the outer tubular section of the mouthpiece and onto the stop to increase the sealing action of the stop.

The stop may be configured to enable a maximum insertion of the inner tubular section of the mouthpiece into the hollow tubular filter portion of the aerosol-generating article of 6 millimeters, preferably 5 millimeters, more preferably around 4 millimeters. An overlap of around 5 millimeters may be provided between the outer tubular section of the mouthpiece and an inserted hollow tubular filter section of an aerosol-generating article.

The insertion distance may be sufficient to secure a firm connection between the aerosol-generating article and the mouthpiece. This may prevent leakage between the aerosol-generating article and the mouthpiece.

The inner tubular section may have an outer diameter of between 2 millimeters and 7 millimeters, preferably between 3.5 millimeters and 4.5 millimeters, more preferably around 4 millimeters.

The outer tubular section may have an inner diameter of between 5 millimeters and 8 millimeters, preferably between 5.5 millimeters and 7 millimeters, more preferably around 6.3 millimeters.

The mouthpiece may comprise a central airflow channel arranged along the longitudinal axis of the mouthpiece.

The central airflow channel may be arranged along the longitudinal axis of the mouthpiece so that, after insertion of the hollow tubular filter portion of the aerosol-generating article between the inner tubular section and the outer tubular section of the mouthpiece, the longitudinal axis of the aerosol-generating article aligns with the longitudinal axis of the mouthpiece. In other words, after connecting the aerosol-generating article to the mouthpiece, the central airflow channel of the mouthpiece preferably is aligned with the aerosol-generating article such that air may be drawn through the aerosol-generating article and into the central channel of the mouthpiece.

The airflow channel may comprise a Venturi portion, wherein the Venturi portion may comprise an inlet portion, an optional central portion and an outlet portion. The inlet portion may be configured converging in a downstream direction and the outlet portion may be configured diverging in a downstream direction. In that way, the optional central portion of the Venturi portion is the portion with the smallest diameter between the inlet portion and the outlet portion. The central portion may have any suitable length, preferably, the central portion has a length of below 4 millimeters. In some embodiments there is no central portion where the inlet portion and the outlet portion abut with each other directly. In this case, the term "central portion" may be used to refer to that cross section of the Venturi portion where the constriction is the smallest, even if physically the inlet portion and the outlet portion touch in that cross section. In these embodiments the length of the central cross section may be in principle zero.

The inner tubular section may comprise an upstream end, and the outer circumference of the upstream end of the inner tubular section may be rounded.

A rounded upstream end of the inner tubular section may facilitate insertion of the mouthpiece into the hollow tubular filter portion of the aerosol-generating article or, respectively, the insertion of the hollow tubular filter portion of the aerosol-generating article between the inner tubular section and the outer tubular section of the mouthpiece.

The outer tubular section may comprise an upstream end, and the inner circumference of the upstream end of the outer tubular section may be tapered.

A tapered upstream end of the outer tubular section may facilitate insertion of the hollow tubular filter portion of the aerosol-generating article between the inner tubular section and the outer tubular section of the mouthpiece. The inner circumference of the outer tubular section may be tapered towards the downstream end of the mouthpiece.

The inner tubular section and the outer tubular section of the mouthpiece may converge towards a downstream end of the mouthpiece such that the hollow tubular filter portion of the aerosol-generating article may be easily inserted between the inner tubular section and the outer tubular section and securely held between the inner tubular section and the outer tubular section during further insertion of the hollow tubular filter portion between the inner tubular section and the outer tubular section. The inner tubular section and the outer tubular section of the mouthpiece preferably form a tubular slot for insertion of the hollow tubular filter portion of the aerosol-generating article. Preferably, the tubular slot has a wide entrance at the upstream end of the mouthpiece for ease of insertion of the hollow tubular filter portion of the aerosol-generating article and narrows down towards the downstream end of the mouthpiece for securely holding the aerosol-generating article. Preferably, the upstream inner diameter of the tubular slot of the mouthpiece, that is, at the outer edge of the tubular slot, is smaller than the inner diameter of the hollow tubular filter portion of the aerosol-generating article. Preferably, the upstream outer diameter of the tubular slot of the mouthpiece that is, at the outer edge of the tubular slot, is larger than the inner diameter of the hollow tubular filter portion of the aerosol-generating article. Preferably, the downstream inner diameter of the tubular slot of the mouthpiece, that is, at the bottom of the tubular slot, is equal to or larger than the inner diameter of the hollow tubular filter portion of the aerosol-generating article. Preferably, the downstream outer diameter of the tubular slot of the mouthpiece, that is, at the bottom of the tubular slot, is smaller than the inner diameter of the hollow tubular filter portion of the aerosol-generating article.

In addition to the secure holding of the aerosol-generating article, leakage of air or aerosol between the aerosol-generating article and the mouthpiece may thus be efficiently prevented, or reduced at least to some extent. Further, the attached aerosol-generating article may be automatically centered due to the attachment with the mouthpiece as described herein with great precision.

The mouthpiece may be configured that after insertion of the hollow tubular filter portion of the aerosol-generating article, the resistance to draw is between 50 millimeter Water Gauge, (mmWG) and 150 mmWG, preferably, the resistance to draw is between 50 mmWG and 70 mmWG.

The outer circumference of the inner tubular section may be conical, and, preferably, the outer diameter of the inner tubular section increases towards a downstream direction.

The inner circumference of the outer tubular section may be conical, and, preferably, the inner diameter of the outer tubular section decreases towards a downstream direction.

The mouthpiece may comprise a hinge section for attachment of the mouthpiece to an aerosol-generating device.

The hinge section may extend perpendicular to the longitudinal axis of the mouthpiece. The hinge section may comprise conventional connection means for connecting the hinge section with an aerosol-generating device. The hinge section may be integrally formed with the mouthpiece. The hinge section may be configured such that the mouthpiece may be pivotably opened to enable the aerosol-generating article to be inserted into the aerosol-generating device. After insertion of the aerosol-generating article, the mouthpiece may be pivotably closed by means of the hinge section. During closing of the mouthpiece with the aerosol-generating device, a connection may be established between the mouthpiece and the aerosol-generating article as described above. Particularly, the aerosol-generating article may be inserted into the aerosol-generating device such that the hollow tubular filter portion of the aerosol-generating article sticks out of the aerosol-generating device in a downstream direction. During closing of the mouthpiece, the tubular filter portion of the aerosol-generating article may be pressed between the inner tubular portion and the outer tubular portion of the mouthpiece to facilitate a secure connection without leakage.

The mouthpiece may be made of one or more of the following materials: ceramic, composite, resin (for example Accura 25); polymeric, Silicon, (soft material) polylactic acid; or an eco-friendly polymeric material, or combinations thereof.

The present invention also relates to an aerosol-generating device comprising a mouthpiece as described herein. The aerosol-generating device may comprise a housing, electric circuitry, a power supply, a heating chamber and a heating element.

As used herein, an 'aerosol-generating device' relates to a device that interacts with an aerosol-forming substrate to generate an aerosol. The aerosol-forming substrate may be part of the aerosol-generating article. An aerosol-generating device may be a device that interacts with an aerosol-forming substrate of the aerosol-generating article to generate an aerosol.

The electric circuitry may comprise a microprocessor, which may be a programmable microprocessor. The microprocessor may be part of a controller. The electric circuitry may comprise further electronic components. The electric circuitry may be configured to regulate a supply of power to the heating element. Power may be supplied to the heating element continuously following activation of the system or may be supplied intermittently, such as on a puff-by-puff basis. The power may be supplied to the heating element in the form of pulses of electrical current. The electric circuitry may be configured to monitor the electrical resistance of the heating element, and preferably to control the supply of power to the heating element dependent on the electrical resistance of the heating element.

The device may comprise a power supply, typically a battery, within the main body. As an alternative, the power supply may be another form of charge storage device such as a capacitor. The power supply may require recharging and may have a capacity that enables to store enough energy for one or more usage experiences; for example, the power supply may have sufficient capacity to continuously generate aerosol for a period of around six minutes or for a period of a multiple of six minutes. In another example, the power supply may have sufficient capacity to create an aerosol for multiple puffs.

The power supply may be any suitable power supply, for example a DC voltage source such as a battery. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

As used herein, the term 'aerosol-generating article' refers to an article comprising an aerosol-forming substrate that is capable of releasing volatile compounds that can form an aerosol, typically under the application of heat, that is, above room temperature. The aerosol-generating article may be disposable.

The hollow tubular filter portion of the aerosol-generating article may comprise for example a hollow acetate tube (HAT), a fine hollow acetate tube (FHAT) or a plug of tow wrapped around a central cardboard tube, all of which structures being known from manufacture of filter elements. The hollow tubular filter portion preferably comprises a hollow central space. The inner tubular portion of the mouthpiece may be insertable into the hollow central space.

The hollow tubular filter portion may be located immediately downstream of the aerosol-forming substrate comprised in the aerosol-generating article and may directly abut the aerosol-forming substrate. The aerosol-generating article may only comprise the substrate portion and the hollow tubular filter portion.

If desired or required, for example to achieve a sufficiently high resistance to draw of the aerosol-generating article, an additional filter section may be included in the aerosol-generating article. Preferably such additional filter section may be included between the substrate portion and the mouth end portion. Preferably, such additional filter section comprises a filtration material such as, for example, cellulose acetate. Preferably, the length of the additional filter section is between about 4 millimeters and about 8 millimeters, preferably, between about 5 millimeters and about 7 millimeters. Preferably, such additional filter section comprises a filtration material such as, for example, cellulose acetate. Preferably, the combined length of the additional filter section and the hollow tubular filter portion is between about 10 millimeters and about 18 millimeters, preferably, about 13 millimeters.

The hollow tubular filter portion may be formed from any suitable material or combination of materials. For example, the hollow tubular filter portion may be formed from one or more materials selected from the group consisting of: cellulose acetate; cardboard; paper, such as crimped heat resistant paper or crimped parchment paper; cotton; viscose; glass fibres; and other polymeric materials, such as low density polyethylene (LDPE). In a preferred embodiment, the hollow tubular filter portion is formed from cellulose acetate.

The hollow tubular filter portion preferably has an external diameter that is approximately equal to the external diameter of the aerosol-generating article.

The hollow tubular filter portion may have an external diameter of between approximately 4 millimeters and approximately 8 millimeters, for example of between approximately 5 millimeters and approximately 6 millimeters, preferably around 5.3 millimeters. The hollow tubular filter portion may have a length of between approximately 10 millimeters and approximately 40 millimeters, preferably, the hollow tubular filter portion has a length of between about 10 millimeters and about 13 millimeters.

The aerosol-generating article may be substantially cylindrical in shape. However, alternatively other cross sections may be used. Indeed, the cross section of the aerosol-generating article may vary along its length, for example by varying the shape of the cross section or the cross sectional dimensions. The aerosol-generating article may be substantially elongate. The aerosol-generating article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length.

The aerosol-generating article may have a total length between 30 millimeters and 60 millimeters, preferably between 40 millimeters and 50 millimeters, more preferably 45 millimeters. The aerosol-generating article may have an external diameter between approximately 4 millimeters and 8 millimeters, preferably between 5 millimeters and 6 millimeters, more preferably around 5.3 millimeters. In one embodiment, the aerosol-generating article has a total length of approximately 45 millimeters. Further, the aerosol-forming substrate may have a length of between 20 millimeters and 55 millimeters. The aerosol-generating article may comprise an outer wrapper, preferably an outer paper wrapper.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of the aerosol-generating article or smoking article.

The aerosol-forming substrate is a substrate capable of releasing volatile compounds that can form an aerosol. The volatile compounds may be released by heating the aerosol-forming substrate. The aerosol-forming substrate may comprise nicotine. The aerosol-forming substrate may comprise plant-based material. The aerosol-forming substrate may comprise tobacco. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material. The aerosol-forming substrate may comprise homogenised plant-based material, including homogenized tobacco, for example made by, for example, a paper making process or a casting process.

The aerosol-forming substrate may comprise at least one aerosol-former. An aerosol-former is any suitable known compound or mixture of compounds that, in use, facilitates formation of a dense and stable aerosol and that is substantially resistant to thermal degradation at the temperature of operation of the system. Suitable aerosol-formers are for example: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Aerosol formers may be polyhydric alcohols or mixtures thereof, such as triethylene glycol, 1,3-butanediol and glycerine. The aerosol-former may be propylene glycol. The aerosol former may comprise both glycerine and propylene glycol.

The heating element may be arranged inside or around the heating chamber for heating the aerosol-generating article insertable into the heating chamber. The heating chamber may be a cavity. Alternatively, or in addition, an internal heating element may be provided, for example a pin or a blade that is inserted for use at least partly into the aerosol-forming substrate.

For example, the device may include an external heater positioned around a perimeter of the heating chamber. An external heater may take any suitable form. For example, an external heater may take the form of one or more flexible heating foils on a dielectric substrate, such as polyimide. The flexible heating foils can be shaped to conform to the perimeter of the heating chamber. Alternatively, an external heater may take the form of a metallic grid or grids, a flexible printed circuit board, a moulded interconnect device (MID), ceramic heater, flexible carbon fibre heater or may be formed using a coating technique, such as plasma vapour deposition, on a suitable shaped substrate. An external heater may also be formed using a metal having a defined relationship between temperature and resistivity. In such an exemplary device, the metal may be formed as a track between two layers of suitable insulating materials. An external heater formed in this manner may be used to both heat and monitor the temperature of the external heater during operation.

The invention also relates to a system comprising a mouthpiece as described above and an aerosol-generating article, wherein the aerosol-generating article comprises a substrate portion containing aerosol-forming substrate and a hollow tubular filter portion, wherein a minimum outer diameter of the inner tubular section of the mouthpiece is smaller than an inner diameter of the hollow tubular filter portion of the aerosol-generating article, and wherein a maximum inner diameter of the outer tubular section of the mouthpiece is larger than an outer diameter of the aerosol-generating article.

The invention also relates to a method for attaching a mouthpiece to a hollow tubular filter portion of an aerosol-generating article, wherein the method comprises:
  i. providing a mouthpiece as described above,
  ii. providing the aerosol-generating article comprising a substrate portion containing aerosol-forming substrate and the hollow tubular filter portion,
  iii. attaching the mouthpiece to the hollow tubular filter portion of the aerosol-generating article by inserting the inner tubular section of the mouthpiece into the hollow tubular filter portion of the aerosol-generating article.

Features described in relation to one aspect may equally be applied to other aspects of the invention.

The invention will be further described, by way of example only, with reference to the accompanying drawings in which.

Figure 1:
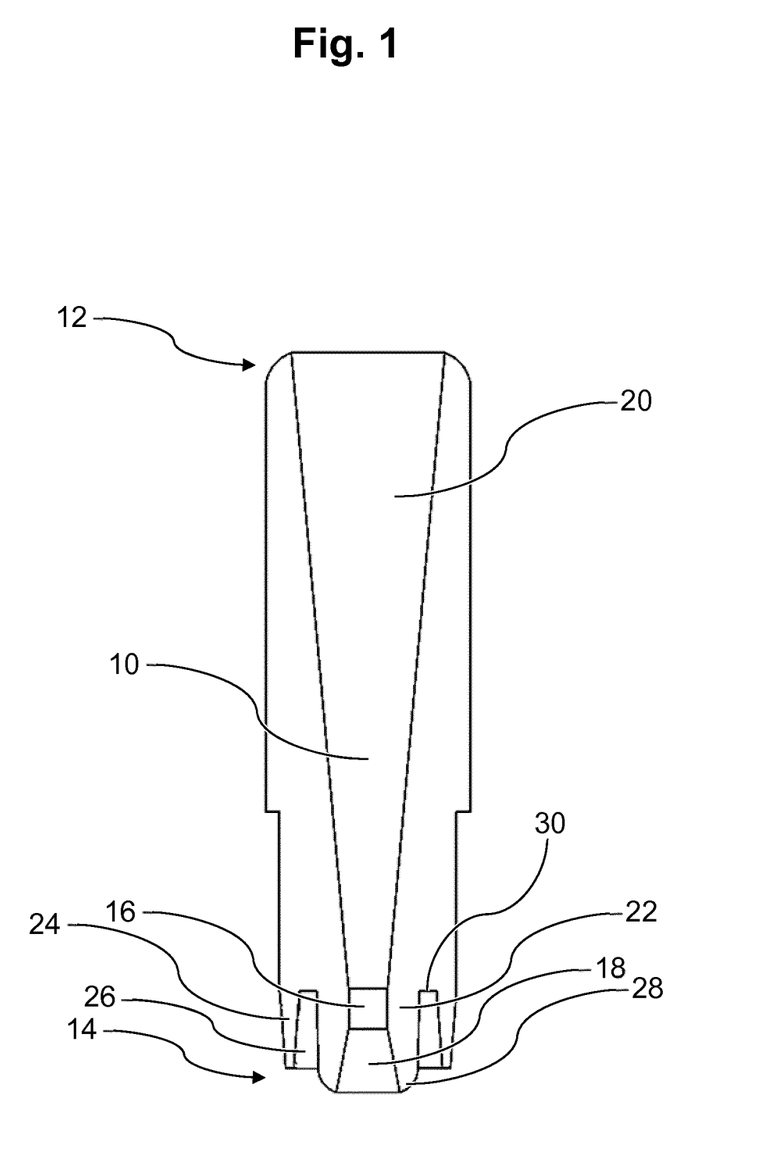
FIG. 1 shows a mouthpiece according to the present invention.

FIG. 1 shows a mouthpiece according to the present invention. The mouthpiece has an elongate shape and comprises a central airflow channel 10 through which air comprising vaporized aerosol-forming substrate can be drawn. The top part of FIG. 1 shows a downstream end 12 of the mouthpiece, while the bottom part of FIG. 1 shows an upstream end 14 of the mouthpiece. Thus, air is drawn, in FIG. 1, from bottom to top.

The mouthpiece shown in FIG. 1 is configured as a Venturi mouthpiece. This means that the central airflow channel 10 has a constricted portion, referred to as central portion 16. Leading towards the central portion 16 from the upstream end 14 is provided an inlet portion 18. Leading away from the central portion 16 towards the downstream end 12 is provided an outlet portion 20. The central portion 16 has a reduced diameter in comparison to the outlet portion 20, which diverges from the central portion 16 towards the downstream end 12. In the outlet portion 20, the airstream expands and cools down so that aerosol droplets can form.

The mouthpiece comprises, at its upstream end 14, a configuration for attachment to an aerosol-generating article, particularly to a hollow tubular filter portion of the aerosol-generating article. At the upstream end 14, the mouthpiece comprises an inner tubular section 22 as well as an outer tubular section 24. The inner tubular section 22 is arranged inside of the outer tubular section 24. Between the inner tubular section 22 and the outer tubular section 24, a tubular slot 26 is provided for insertion of the hollow tubular filter portion of the aerosol-generating article.

The inner tubular section 22 of the mouthpiece has a minimum outer diameter which is smaller than the inner diameter of the hollow tubular filter portion. The outer tubular section 24 has a maximum inner diameter which is larger than the outer diameter of the hollow tubular filter portion. Preferably, the inner tubular section 22 is tapered towards the upstream end 14 and the outer tubular section 24 is tapered towards the downstream end 12. Hence, a conical shape of the tubular slot 26 is created for simplifying insertion of the hollow tubular filter portion. In addition, the inner tubular section 22 may comprise a rounded upstream end 28 for facilitating insertion into the hollow tubular filter portion of the aerosol-generating article to be attached.

The mouthpiece comprises a stop 30 configured connecting the inner tubular section 22 and the outer tubular section 24 so that the hollow tubular filter portion can only be inserted into the tubular slot 26 up to the stop 30. When the hollow tubular filter portion of the aerosol-generating article is fully inserted into the tubular slot 26, the aerosol-generating article is securely held within the tubular slot 26 and therefore connected with the mouthpiece. After full insertion, the hollow tubular filter portion may overlap with the outer tubular section 24 by around 5 millimeters.

Figure 2:
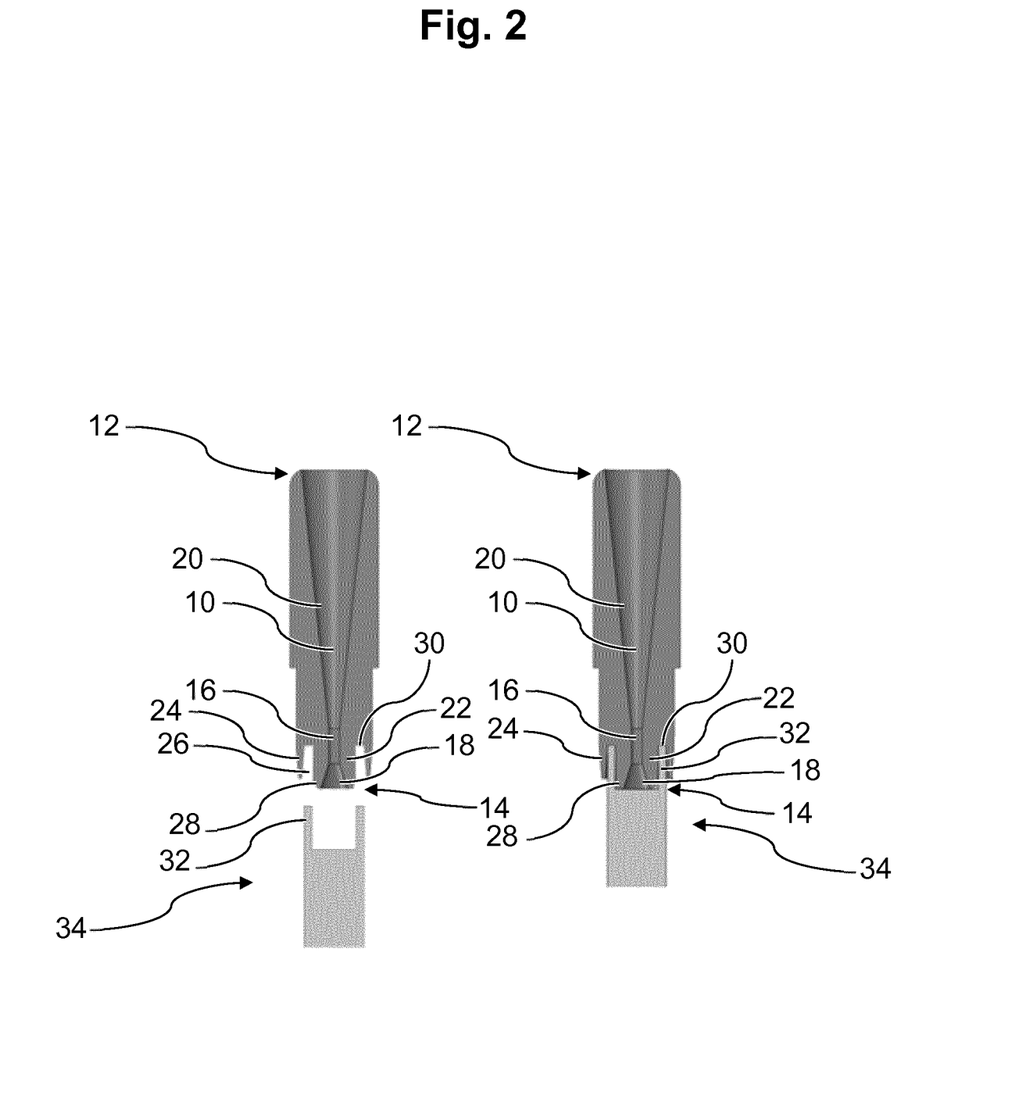
FIG. 2 shows the connection of a hollow tubular filter portion of an aerosol-generating article with the mouthpiece.

FIG. 2 shows the operation of inserting the hollow tubular filter portion 32 of the aerosol-generating article 34 into the mouthpiece or, respectively, attaching the mouthpiece to the aerosol-generating article 34. In the left part of FIG. 2, the aerosol-generating article 34 is depicted before connection between the mouthpiece and the aerosol-generating article 34 is established. In the right part of FIG. 2, the hollow tubular filter portion 32 of the aerosol-generating article 34 has been pushed into the tubular slot 26 of the mouthpiece so that a connection between the mouthpiece and the aerosol-generating article 34 has been established.

Figure 3:
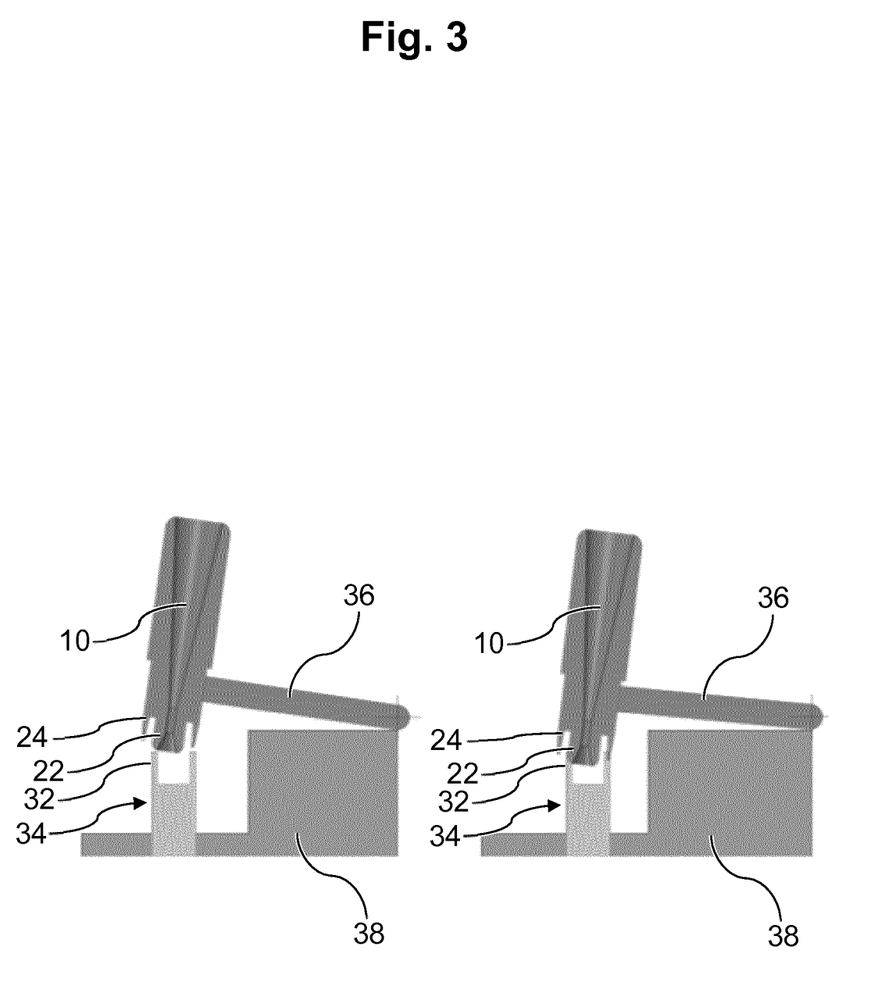
FIG. 3 shows a hinge section of the mouthpiece for connection with an aerosol-generating device.

FIG. 3 shows a hinge section 36 of the mouthpiece for pivotably opening and closing the mouthpiece for attachment or detachment from the aerosol-generating article 34. The hinge section 36 may be connected or may be configured connectable with an aerosol-generating device so that the mouthpiece may be provided as part of the aerosol-generating device. Before a use, the mouthpiece may be pivotably opened by means of the hinge section 36. Subsequently, the aerosol-generating article 34 may be inserted into a heating chamber of the aerosol-generating device. Then, the mouthpiece may be pivotably closed and a connection between the mouthpiece and the aerosol-generating article 34 established as for example depicted in FIG. 2. FIG. 3 shows two points in time during a joining operation. In the left part of FIG. 3, the hinge section 36 is closed, but not yet fully closed. In the right part of FIG. 3, the closing has not yet been completed, but the hinge section 36 is pivoted further towards a closing position in comparison with the left part of FIG. 3. After a smoking experience, the mouthpiece may again be pivotably opened and the spent aerosol-generating article 34 be removed from the mouthpiece and afterwards from the heating chamber of the aerosol-generating device.

Figure 4:
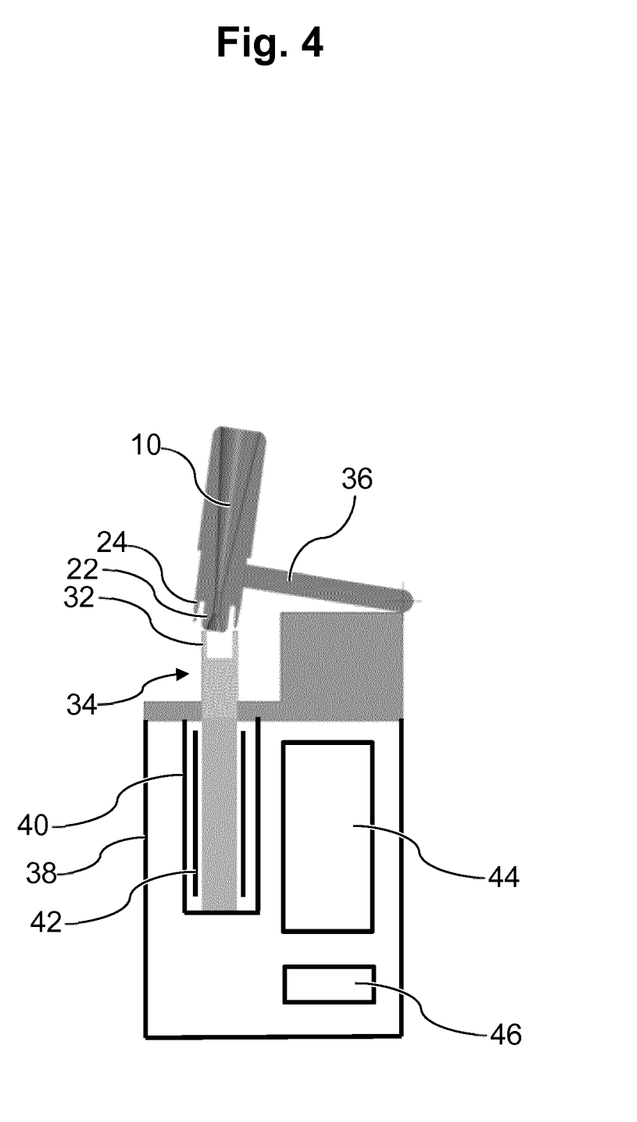
FIG. 4 shows an aerosol-generating device comprising the mouthpiece and an aerosol-generating article inserted into a heating chamber of the aerosol-generating device.

FIG. 4 shows an aerosol-generating device 38 comprising a heating chamber 40 for insertion of the aerosol-generating article 34 as well as further components of the aerosol-generating device 38. Also, FIG. 4 shows the mouthpiece connected to the aerosol-generating device 38 by means of the hinge section 36 described in connection with FIG. 3. The aerosol-generating device 38 comprises further components such as a heating element 42, a power supply 44 for supplying electrical energy to the heating element 42 and electric circuitry 46 for controlling the supply of electrical energy from the power supply 44 to the heating element 42.

The invention claimed is:

1. A mouthpiece for attachment to a hollow tubular filter portion of an aerosol-generating article, the mouthpiece comprising:
   an inner tubular section having a minimum outer diameter, which is smaller than an inner diameter of the hollow tubular filter portion of the aerosol-generating article;
   an outer tubular section having a maximum inner diameter, which is larger than an outer diameter of the aerosol-generating article;
   a central airflow channel arranged along a longitudinal axis of the mouthpiece,
      wherein the airflow channel comprises a Venturi portion,
      wherein the Venturi portion comprises an inlet portion and an outlet portion,
      wherein the inlet portion is configured to converge in a downstream direction and the outlet portion is configured to diverge in a downstream direction; and
   a hinge section configured to attach the mouthpiece to an aerosol-generating device.

2. The mouthpiece according to claim 1, wherein the Venturi portion further comprises a central portion.

3. The mouthpiece according to claim 1, further comprising a stop arranged connecting the inner tubular section and the outer tubular section.

4. The mouthpiece according to claim 3, wherein the stop is configured to enable a maximum insertion of the inner tubular section of the mouthpiece into the hollow tubular filter portion of the aerosol-generating article of 6 millimeters.

5. The mouthpiece according to claim 3, wherein the stop is configured to enable a maximum insertion of the inner tubular section of the mouthpiece into the hollow tubular filter portion of the aerosol-generating article of around 4 millimeters.

6. The mouthpiece according to claim 1, wherein the inner tubular section has an outer diameter of between 3 millimeters and 5 millimeters.

7. The mouthpiece according to claim 1, wherein the inner tubular section has an outer diameter of around 4 millimeters.

8. The mouthpiece according to claim 1, wherein the outer tubular section has an inner diameter of between 5 millimeters and 8 millimeters.

9. The mouthpiece according to claim 1, wherein the outer tubular section has an inner diameter of around 6.3 millimeters.

10. The mouthpiece according to claim 1,
    wherein the inner tubular section comprises an upstream end, and
    wherein the outer circumference of the upstream end of the inner tubular section is rounded.

11. The mouthpiece according to claim 1,
    wherein the outer tubular section comprises an upstream end, and
    wherein the inner circumference of the upstream end of the outer tubular section is tapered.

12. The mouthpiece according to claim 1,
    wherein the outer circumference of the inner tubular section is conical, and
    wherein the outer diameter of the inner tubular section increases towards a downstream direction.

13. The mouthpiece according to claim 1,
wherein the inner circumference of the outer tubular section is conical, and
wherein the inner diameter of the outer tubular section decreases towards a downstream direction.

14. The mouthpiece according to claim 1,
wherein the inner tubular section and the outer tubular section of the mouthpiece are configured to form a tubular slot between the inner tubular section and the outer tubular section, and
wherein the tubular slot is configured to securely receive and hold the hollow tubular filter portion of the aerosol-generating article.

15. A system comprising a mouthpiece according to claim 1 and an aerosol-generating article,
wherein the aerosol-generating article comprises a substrate portion containing aerosol-forming substrate and a hollow tubular filter portion,
wherein a minimum outer diameter of the inner tubular section of the mouthpiece is smaller than an inner diameter of the hollow tubular filter portion of the aerosol-generating article, and
wherein a maximum inner diameter of the outer tubular section of the mouthpiece is larger than an outer diameter of the aerosol-generating article.

16. A method for attaching a mouthpiece to a hollow tubular filter portion of an aerosol-generating article, the method comprising:
providing a mouthpiece according to claim 1;
providing the aerosol-generating article comprising a substrate portion containing aerosol-forming substrate and the hollow tubular filter portion; and
attaching the mouthpiece to the hollow tubular filter portion of the aerosol-generating article by inserting the inner tubular section of the mouthpiece into the hollow tubular filter portion of the aerosol-generating article.

* * * * *